United States Patent [19]
Stone et al.

[11] Patent Number: 5,253,655
[45] Date of Patent: Oct. 19, 1993

[54] APPARATUS AND METHOD FOR MEASURING RANGE OF MOTION OF AN ARTICULATED JOINT

[76] Inventors: Kevin R. Stone, 1 Throckmorton La., Mill Valley, Calif. 94941; Perry A. Klebahn, 2633 Steiner St., San Francisco, Calif. 94115; William R. Knapp, 116 Gilbert St., Menlo Park, Calif. 94025

[21] Appl. No.: 992,066
[22] Filed: Dec. 17, 1992
[51] Int. Cl.$^5$ .............................................. A61B 5/10
[52] U.S. Cl. ..................................... 128/782; 33/755
[58] Field of Search ............... 128/774, 782; 73/865.4; 33/421, 453, 755, 759, 511, 512

[56] References Cited

U.S. PATENT DOCUMENTS

| | | | |
|---|---|---|---|
| 1,590,499 | 6/1926 | Cozad . | |
| 1,612,637 | 12/1926 | Mesteston | 33/755 |
| 2,565,381 | 8/1951 | Leighton | 33/221 |
| 3,020,639 | 2/1962 | Karpovich et al. | 33/1 |
| 3,229,372 | 1/1966 | Quashnock et al. | 33/75 |
| 4,201,226 | 5/1980 | Phillips | 128/774 |
| 4,306,571 | 12/1981 | McLeod, Jr. | 128/782 |
| 4,461,085 | 7/1984 | Dewar et al. | 33/174 |
| 4,485,825 | 12/1984 | Domjan et al. | 128/774 |
| 4,583,555 | 4/1986 | Malcom et al. | 128/774 |
| 4,712,542 | 12/1987 | Daniel et al. | 128/92 |
| 4,779,212 | 10/1988 | Levy | 33/755 |
| 4,804,001 | 2/1989 | McLeod, Jr. | 128/782 |
| 4,834,057 | 5/1989 | McLeod, Jr. | 128/782 |
| 4,911,177 | 3/1990 | Lamb et al. | 128/782 |
| 4,969,471 | 11/1990 | Daniel et al. | 128/774 |
| 5,142,793 | 9/1992 | Crane | 33/755 |

FOREIGN PATENT DOCUMENTS 55-95804  7/1980  Japan .

OTHER PUBLICATIONS

Townsend et al., "Total Motion knee Goniometry," J. Biomechanics, vol. 10, No. 3, pp. 183-193.
Chao et al., "Instrumented Measurement of Human Joint Motion," ISA Transactions, vol. 17, No. 1, pp. 13-19 1978.
Kettelkamp et al., "An Electrogoniometric Study of Knee Motion in Normal Gait," The Journal of Bone and Joint Surgery, vol. 52-A, No. 4, pp. 775-790 Jun. 1970.

Primary Examiner—Max Hindenburg
Attorney, Agent, or Firm—Lahive & Cockfield

[57] ABSTRACT

An apparatus for measuring the angle A of flexure of a joint between longitudinal axes of adjacent, jointed body parts includes first and second coupling mechanisms for fixture respectively to the first and second body parts. Each of the coupling mechanisms is fixed to its respective body part at a specified distance from the joint being measured. The apparatus further includes a measuring device for generating a signal representative of the direct, linear distance between the coupling mechanisms as the joint passes through a range of motion. A computing device operates in response to the signal generated by the measuring device to determine the angle A in accordance with the law of cosines. An advantage of the apparatus is that it is significantly tolerant of improper placement of the coupling mechanisms.

12 Claims, 2 Drawing Sheets

ANGLE (A)

| THIGH RATIOS - L1/(L1+L2) | 10 | 20 | 30 | 40 | 50 | 60 | 70 | 80 | 90 |
|---|---|---|---|---|---|---|---|---|---|
| 0.5 | 99.62% | 98.48% | 96.59% | 93.97% | 90.63% | 86.60% | 81.92% | 76.60% | 70.71% |
| 0.49 | 99.62% | 98.48% | 96.59% | 93.97% | 90.63% | 86.61% | 81.92% | 76.62% | 70.72% |
| 0.48 | 99.62% | 98.48% | 96.60% | 93.98% | 90.65% | 86.63% | 81.95% | 76.65% | 70.77% |
| 0.47 | 99.62% | 98.49% | 96.61% | 93.99% | 90.67% | 86.65% | 81.99% | 76.70% | 70.84% |
| 0.46 | 99.62% | 98.49% | 96.61% | 94.01% | 90.69% | 86.69% | 82.04% | 76.78% | 70.94% |
| 0.45 | 99.62% | 98.50% | 96.63% | 94.03% | 90.73% | 86.75% | 82.12% | 76.87% | 71.06% |
| 0.44 | 99.62% | 98.50% | 96.64% | 94.06% | 90.77% | 86.81% | 82.20% | 76.99% | 71.22% |
| 0.43 | 99.63% | 98.51% | 96.66% | 94.09% | 90.82% | 86.89% | 82.31% | 77.13% | 71.40% |
| 0.42 | 99.63% | 98.52% | 96.68% | 94.13% | 90.88% | 86.97% | 82.43% | 77.29% | 71.61% |
| 0.41 | 99.63% | 98.53% | 96.70% | 94.17% | 90.95% | 87.07% | 82.56% | 77.47% | 71.85% |
| 0.4 | 99.63% | 98.54% | 96.73% | 94.22% | 91.02% | 87.18% | 82.71% | 77.68% | 72.11% |
| 0.39 | 99.64% | 98.55% | 96.76% | 94.27% | 91.11% | 87.30% | 82.88% | 77.90% | 72.40% |
| 0.38 | 99.64% | 98.57% | 96.79% | 94.33% | 91.20% | 87.43% | 83.06% | 78.14% | 72.72% |
| 0.37 | 99.65% | 98.58% | 96.83% | 94.39% | 91.29% | 87.57% | 83.26% | 78.41% | 73.06% |
| 0.36 | 99.65% | 98.60% | 96.86% | 94.46% | 91.40% | 87.73% | 83.47% | 78.69% | 73.43% |
| 0.35 | 99.65% | 98.62% | 96.90% | 94.53% | 91.51% | 87.89% | 83.70% | 78.99% | 73.82% |
| 0.34 | 99.66% | 98.64% | 96.95% | 94.60% | 91.63% | 88.07% | 83.95% | 79.32% | 74.24% |
| 0.33 | 99.66% | 98.66% | 96.99% | 94.69% | 91.76% | 88.26% | 84.20% | 79.66% | 74.69% |
| 0.32 | 99.67% | 98.68% | 97.04% | 94.77% | 91.90% | 88.45% | 84.48% | 80.02% | 75.15% |
| 0.31 | 99.67% | 98.70% | 97.09% | 94.86% | 92.04% | 88.66% | 84.77% | 80.40% | 75.64% |
| 0.3 | 99.68% | 98.73% | 97.15% | 94.96% | 92.19% | 88.88% | 85.07% | 80.80% | 76.16% |

% OF STRAIGHT LEG LENGTH

APPARATUS AND METHOD FOR MEASURING RANGE OF MOTION OF AN ARTICULATED JOINT

BACKGROUND OF THE INVENTION

The invention relates generally to an apparatus for measuring the range of motion of an articulated joint. In particular, the invention concerns a device for determining the flexure angle between adjacent, jointed body parts, as a function of the linear distance between two points, one each located on each of the body parts.

Arthrometers measure joint motion. Generally, two types of arthrometers are currently available: passive arthrometers for measuring joint motion of another person, and automatic arthrometers for measuring one's own joint motion. Typically, passive arthrometers are referred to as goniometers.

The need to measure joint motion frequently occurs during rehabilitation therapy. For example, patients participating in post-operative therapy following knee surgery are often instructed to perform standing or supine knee-bends from between thirty to eighty degrees. Once such a patient is discharged from the hospital and large, complex automatic arthrometers are no longer available to the patient, the actual flexure angle is typically determined by mere guesswork.

Simple, automatic measurement of joint motion during exercise has not been heretofore available. Neither has there been available mechanisms for indicating actual range of motion and counting repetitions in an exercising cycle. Accordingly, individuals who have been discharged from a health care facility and instructed to maintain a therapeutic exercise regimen, have been faced with great difficulty in implementing that regimen.

It is an object of the invention, therefore, to provide a simple device for measuring joint motion which is easily used by an unskilled operator. Another object of the invention is to provide such a device which is able to compensate for improper arrangement about a user's joint. Yet another object of the invention is to provide a device for measuring joint motion and for counting cycles in an exercise regimen.

SUMMARY OF THE INVENTION

These and other objects are achieved by the present invention which in one aspect features an apparatus for measuring the angle between longitudinal axes of adjacent, jointed body parts. For example, in one embodiment the apparatus measures and provides a signal representative of the angle between the femur of a user's upper leg and the tibia of the patient's lower leg. It can also be adapted for measuring the angle between the humerus of the upper arm and the ulna of the lower arm, as well as for other uses which will be apparent from the description of the invention contained herein.

The apparatus includes a coupling mechanism for fixture to one of the body parts at a specified distance from the joint being measured. A second coupling mechanism is provided for fixture to the other of the body parts, also at a specified distance from the joint being measured. A measuring device, such as a retractable, spirally wound tape, extends between the coupling mechanisms. The measuring device provides a signal indicative of the distance along a straight line between the coupling mechanisms. This distance is a function of the angle of flexure of the joint between the body parts to which the coupling mechanisms are fixed.

The apparatus further includes a computing device for determining the angle of flexure of the joint as a function of the distance between the coupling mechanisms as indicated by the measuring device. It has been found that the angle of flexure can be determined as a trigonometric function of the distance between each coupling mechanism and the joint being measured, and the linear distance between the coupling mechanisms.

A significant advantage of the invention is that it has been found that the linear distance between the coupling mechanisms substantially dominates the trigonometric function which reveals the angle of flexure of the joint being measured. Accordingly, the inventive apparatus is significantly tolerant of variation in the distance between each coupling mechanisms and the joint being measured. For example, as will be described below in greater detail, experimentation has shown that as much as a 40% error in the placement of the coupling mechanisms, results in only approximately 5% error in joint flexure measurement. At a joint flexure of 90°, 5% error represents a reading error of only approximately 4.5°. Moreover, natural human proportions make nearly impossible, a coupling mechanism placement error of as great as 40%.

In another aspect, the invention features a method for measuring the angle between the longitudinal axes of adjacent, jointed body parts. The method includes the steps of attaching one end of a retractable measuring device to one of the body parts, such as the femur of the upper leg, and the other end of the device to the other of the body parts, such as the ankle at the base of the tibia of the lower leg. A calibration step then includes the measurement of the distance between the ends of the measuring device when the angle being measured is visually estimated to be approximately 180°. The angle of flexure of the joint between the body parts can then be monitored as a trigonometric function of the linear distance between the ends of the measuring device as the joint passes through a specified range of motion.

These and other features of the invention will be more fully appreciated by referral to the following detailed description which is to be read in conjunction with the attached drawing in which the same reference numbers refer to the same elements throughout the several views.

BRIEF DESCRIPTION OF THE DRAWINGS

The foregoing and other objects of this invention, the various features thereof, as well as the invention itself, may be more fully understood from the following description, when read together with the accompanying drawings in which:

FIG. 3 is a chart showing normal distances between hip and ankle for adult human beings as a function of knee joint angle for various thigh ratios.

DETAILED DESCRIPTION

In one aspect, the invention features a method for measuring the angle between longitudinal axes of adjacent, jointed body parts. This is achieved through the recognition that the angle operates as a trigonometric function of distances between specified points along the body parts and the joint being measured, as well as the linear distance between the specified points.

Figure 1:
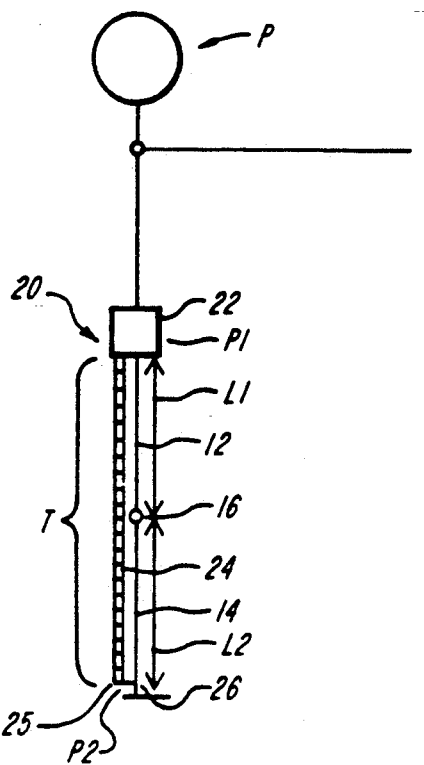
FIG. 1 is a schematic view representative of a user employing a device constructed in accordance with the teachings of the present invention, the user standing in an fully upright position.
Figure 2:
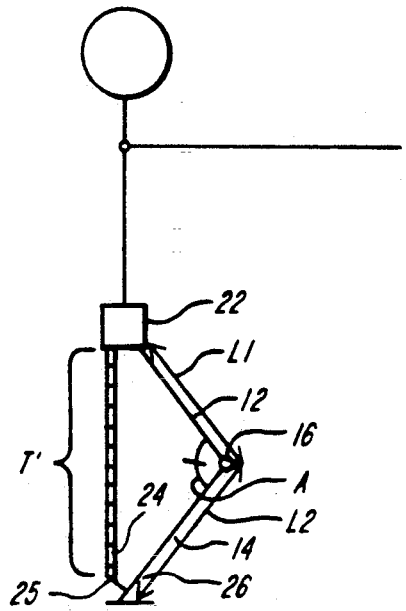
FIG. 2 is a schematic view representative of a user employing the device depicted in FIG. 1, the user maintaining a partial knee-bend position.

As schematically represented in FIGS. 1 and 2, in one embodiment the inventive device 20 can be utilized to determine the angle A between the femur 12 of a user's upper leg and the tibia 14 of the user's lower leg. More commonly, the angle A is recognized as the angle of flexure of the user's knee 16. Though not described herein in great detail, it should be recognized that the device can be readily adapted for determining the angle of flexure of other jointed body parts such the elbow joint between a user's upper and lower arm.

In the illustrated embodiment, the device 20 includes a console (or housing) 22 and a measuring device 24 (such as a length-calibrated tape or cord). The console 22 is coupled to the user's upper leg 12, preferably near the hip, and a distal end 25 of the measuring device 24 is coupled to the user's lower leg 14, preferably at the end, such as at the ankle 26. Although it is preferable that console 22 and distal end 25 are coupled near the ends of the user's respective leg portions, the points of coupling may alternatively be at other points along the user's leg. A variety of coupling mechanisms are suitable for this purpose. For example hook and loop type fastening systems, such as the Velcro brand which is commonly known, as well as snapped or buckled straps will function sufficiently. Other, ordinarily known coupling mechanisms will be readily apparent as well.

The measuring device 24 is retractable into the console 22 so that as the user bends her knee 16 through a range of motion, thereby reducing the distance between the console 22 and the end 25 of the measuring device 24, the measuring device 24 retracts into the console 22. A variety of commonly known devices are suitable for this purpose. For example, a spirally wound tape device such as is typically referred to a carpenter's tape measure can be used. In the preferred embodiment, the console includes a device for generating a signal representative of the length T of measuring device 24 that extends from the console 22.

The console 22 includes a computing device which has a processing unit for interpreting the signal received from the measuring device 24 to determine the angle A. The signal can be generated in a variety of ways. For example, the measuring device 24 can be spirally wound around a roller (not shown) which is attached to a potentiometer or digital encoder wheel (also not shown). The linear extension of the measuring device 24 can then be determined as a function of the number of revolutions of the roller.

However it is determined, the length of the extension of the measuring device 24 is translatable into the angle A. This is done by first calibrating the device to determine the total distance T between the console 22 and the end 25 of the measuring device 24. Based on what has been determined to be a fairly universal "thigh ratio" for the human race at large, a distance L1 between the console 22 and the knee 16, and a distance L2 between the end 25 of the tape device 24 can be determined from the total distance T. This universal thigh ratio, which is 0.5, is the ratio of the distance L1 to the distance T. Calibration of the device is made with the user standing in an upright position as shown in FIG. 1.

It can be seen from FIG. 2 that as the user flexes her knee 16, the distances L1 and L2 remain constant while the distance T is reduced. It can also be seen that these three lengths together form a triangle. Since of these three triangle legs, only distance T changes, the law of cosines can be applied to determine the angle A as a function of the distance T.

According to the law of cosines, angle A can be determined by the following relationship.

$$A = \cos^{-1}[(L1^2 + L2^2 - T^2)/2(L1)(L2)]$$

FIG. 3 is a chart reflecting that there is a relatively small error in detection of the angle A which corresponds to somewhat large errors in the placement of the console 22 on a user's thigh 12 (or the measurement of L1 and/or L2). Each column of the chart represent values for the distance between console 22 and the end 25 of measuring device 24 for an indicated angle of flexure, and different thigh ratios resulting from various thigh ratios in adult human beings between the hip and knee joint. Each row of the chart represents values for a specified thigh ratio, over a range of flexure angles. The values shown in the body of the chart represent the percentage of the straight leg length T, that the bent leg length T' is.

The top row of the chart in FIG. 3 shows for the indicated degrees of flexure angle, the percentage of T which T' will be, based on the law of cosines, at a thigh ratio of 0.5 (namely, L1 equal to L2). In the other rows, the chart shows the error which is associated with varying degrees of actual thigh ratio based on a user's improper arrangement of the console 22, either by placement of console 22 other than at the hip or by placement of the end 25 of measuring device 24 other than at the ankle, or a combination of such placements. It can be seen, then, that in the case of a 10° flexure angle, improper placement of the console 22 causing as great as a 40% error in thigh ratio (an actual thigh ratio of 0.3), results in a reading of the ratio of T' to T which is only off by approximately 0.06% of the length T. At 90° of flexure, the same improper console placement results in a reading of the ratio of T' to T which is off by 5.45% of the length T. This translates to an error of merely approximately 5° in the reading of angle A.

In view of the insensitivity of the computed angle A to the values for L1 and L2 (due to placement error, or thigh ratio variation), the angle A can be approximated from a computation of $$A = \cos^{-1}[1 - 2(T/T_o)^2]$$

where $T_o$ is the distance T when A = 180 degrees (i.e. $T_o = L1 + L2$), and where L1 substantially equals L2, e.g. as shown in FIG. 3.

The processing unit in the console can be programmed for a variety of features including the displaying of the flexure angle A, providing an audible signal upon achievement of a specified degree of flexure, prevention of further extension of the measuring device 24 upon achievement of a specified degree of flexure to prevent over flexure, and counting of flexure cycles. Other features will be apparent as well.

Accordingly, while various specified embodiments have been set forth herein with particular detail, many alterations to those embodiments will be apparent to those skilled in the art and are intended to be embraced within the spirit and scope of the invention. The invention is to be defined, therefore, not by the preceding description, but by the claims that follow.

What is claimed is:

1. Apparatus for measuring the angle A of flexure of a joint between longitudinal axes of adjacent, jointed body parts, the apparatus comprising:
   A. first coupling means for fixture to a first of said body parts at a point P1, said point P1 being a distance L1 from the joint being measured;
   B. second coupling means for fixture to a second of said body parts at a point P2, said point P2 being a distance L2 from said joint being measured;
   C. measuring means for generating a signal T representative of the distance between point P1 and point P2;
   D. computing device responsive to said signal from said measuring means including means for determining the angle A in accordance with the function $$A = \cos^{-1}[(L1^2 + L2^2 - T^2)/2(L1)(L2)].$$

2. Apparatus according to claim 1 wherein said measuring means includes:
   i. a retractable spirally wound tape within a housing pivotally coupled to said first coupling means, said tape being spirally wound about a pin and having one end affixed to said pin and its other end extending from said housing and affixed to said second coupling means, and said tape being spring biased toward winding about said pin,
   ii. means for generating said signal representative of the length of said tape unwound from about said pin.

3. Apparatus as set forth in claim 2 wherein said first and second body parts are respectively a user's upper leg and said user's lower leg and the being measured is the knee joint between said upper and lower leg.

4. Apparatus as set forth in claim 1 further comprising means responsive to said computing device for generating a visual display representative of said angle A.

5. Method for measuring the angle A of flexure of a joint between the longitudinal axes of adjacent, jointed body parts, the method comprising the steps of:
   A. providing a measuring device having a free distal end of a spring-loaded retractable tape extending a distince T therefrom;
   B. attaching said measuring device to a first of said body parts at a point P1 separated by a distance L1 from the joint being measured;
   C. attaching said free distal end to a second of said body parts at a point P2 near the end of said second body part;
   D. adjusting the relative position of said first and second body parts so that angle A is substantially equal to 180 degrees;
   E. measuring the distance between P1 and P2 by measuring the length T of said measuring device;
   F. readjusting the relative position of said first and second body parts as desired, and in response to such readjustment monitoring the length T of said measuring device between P1 and P2;
   G. computing the angle A in accordance with the function $$A = \cos^{-1}[(L1^2 + L2^2 - T^2)/2(L1)(L2)].$$

6. Method as set forth in claim 5 wherein said first and second body parts are respectively a user's upper leg and said user's lower leg and the joint being measured is the knee joint between said upper and lower leg.

7. Apparatus for measuring the angle A of flexure of a joint between longitudinal axes of adjacent, jointed body parts, the apparatus comprising:
   A. first coupling means for fixture to a first of said body parts at a point P1, said point P1 being a distance L1 from the joint being measured;
   B. second coupling means for fixture to a second of said body parts at a point P2, said point P2 being a distance L2 from said joint being measured;
   C. measuring means for generating a signal T representative of the distance between point P1 and point P2;
   D. computing device responsive to said signal from said measuring means including means for determining the angle A in accordance with the function $$A = \cos^{-1}[1 - 2(T/T_o)^2]$$

where $T_o = L1 + L2$ and L1 substantially equals L2.

8. Apparatus according to claim 7 wherein said measuring means includes:
   i. a retractable spirally wound tape within a housing pivotally coupled to said first coupling means, said tape being spirally wound about a pin and having one end affixed to said pin and its other end extending from said housing and affixed to said second coupling means, and said tape being spring biased toward winding about said pin,
   ii. means for generating said signal representative of the length of said tape unwound from about said pin.

9. Apparatus as set forth in claim 8 wherein said first and second body parts are respectively a user's upper leg and said user's lower leg and the joint being measured is the knee joint between said upper and lower leg.

10. Apparatus as set forth in claim 9 further comprising means responsive to said computing device for generating a visual display representative of said angle A.

11. Method for measuring the angle A of flexure of a joint between the longitudinal axes of adjacent, jointed body parts, the method comprising the steps of:
    A. providing a measuring device having a free distal end of a spring-loaded retractable tape extending a distince T therefrom;
    B. attaching said measuring device to a first of said body parts at a point P1 separated by a distance L1 from the joint being measured;
    C. attaching said free distal end to a second of said body parts at a point P2 near the end of said second body part;
    D. adjusting the relative position of said first and second body parts so that angle A is substantially equal to 180 degrees;
    E. measuring the distance between P1 and P2 by measuring the length T of said measuring device;
    F. readjusting the relative position of said first and second body parts as desired, and in response to such readjustment monitoring the length T of said measuring device between P1 and P2;
    G. computing the angle A in accordance with the function $$A = \cos^{-1}[1 - (T/T_o)^2]$$

where $T_o = L1 + L2$.

12. Method as set forth in claim 11 wherein said first and second body parts are respectively a user's upper leg and said user's lower leg and the joint being measured is the knee joint between said upper and lower leg.

* * * * *